US00PP15997P3

(12) United States Plant Patent
Larsen

(10) Patent No.: US PP15,997 P3
(45) Date of Patent: Sep. 27, 2005

(54) ***OSTEOSPERMUM* PLANT NAMED 'SUNNY ZARA'**

(50) Latin Name: *Osteospermum eclonis*
Varietal Denomination: Sunny Zara

(75) Inventor: Bjarne N. Larsen, Odense N (DK)

(73) Assignee: Sunny Gronnegyden APS (DK)

( * ) Notice: Subject to any disclaimer, the term of this patent is extended or adjusted under 35 U.S.C. 154(b) by 73 days.

(21) Appl. No.: 10/788,364

(22) Filed: Mar. 1, 2004

(65) Prior Publication Data

US 2004/0194186 P1 Sep. 30, 2004

(51) Int. Cl.[7] ..... A01H 5/00
(52) U.S. Cl. ..... Plt./360
(58) Field of Search ..... Plt./360

(56) References Cited

PUBLICATIONS

UPOV–ROM GTITM, Plant Variety Database, 2004/04, GTI Jouve Retrival Software, Citation for *Osteospermum* 'Sunny Zara'.*

* cited by examiner

*Primary Examiner*—Anne Marie Grunberg
*Assistant Examiner*—June Hwu
(74) *Attorney, Agent, or Firm*—Foley & Lardner, LLP

(57) ABSTRACT

A new distinct cultivar of *Osteospermum* plant named 'Sunny Zara', characterized by its red-purple flower color RHS 59C with stripes of RHS N57B; dense and bushy plant form; with globular plant habit; vigorous growth habit, but less need for chemical growth retardation; and obovate to lanceolate leaves.

4 Drawing Sheets

Genus and species of the plant claimed: *Osteospermum eclonis* (DC) T. Norl.
Variety denomination: Sunny Zara.

BACKGROUND OF THE INVENTION

The present Invention relates to a new and distinct cultivar of *Osteospermum* plant, botanically known as *Osteospermum eclonis* (DC) T. Norl., commonly known by the name Cape Daisy, and hereinafter referred to by the name 'Sunny Zara'.

The new *Osteospermum* is a product of a planned breeding program conducted by the Inventor, Bjarne Larsen, in Stige, Denmark. The new *Osteospermum* originated from a cross made in 2000 by the Inventor between *Osteospermum eclonis* (DC) T. Norl. seedling designated '2.97.96' (unpatented) and *Osteospermum eclonis* (DC) T. Norl. seedling designated '2.290.98' (unpatented). The Inventor selected the new *Osteospermum* cultivar from the progeny of the above crossing in 2002 on the basis of its flower color and compact, freely branching habit. Plants of the new *Osteospermum* are more upright, compact and have a unique color combination of upper and underside of the ray petals.

Asexual reproduction of the new cultivar by terminal vegetative cuttings taken and propagated during trial production batches in Stige, Denmark, has shown that the unique features of this new *Osteospermum* are stable and reproduced true to type in many successive generations.

BRIEF SUMMARY OF THE INVENTION

Plants of the cultivar 'Sunny Zara' have not been observed under all possible environmental conditions. The phenotype may vary somewhat with variations in environment such as temperature, light intensity, day length, and fertility level without, however, any variance in genotype.

The following traits have been repeatedly observed and are determined to be the unique characteristics of 'Sunny Zara'. These characteristics in combination distinguish 'Sunny Zara' as a new and distinct cultivar:

1. Red-purple flower color RHS 59C with stripes of RHS N57B.
2. Dense and bushy plant form; with globular plant habit.
3. Vigorous growth habit, but less need for chemical growth retardation.
4. Obovate to lanceolate leaves.

Plants of the cultivar 'Sunny Zara' can be compared to plants of the *Osteospermum eclonis* (DC) T. Norl. cultivar 'Sunny Sonja' (U.S. Plant Pat. No. 10,341). In side-by-side comparisons conducted by the Inventor in Stige Denmark, plants of the cultivar 'Sunny Zara' and the cultivar 'Sunny Sonja' differ in the following characteristics:

1. 'Sunny Zara' has red-purple flower color RHS 59C with stripes of RHS N57B, while 'Sunny Sonja' has dark purple flower color, near RHS 77B and 78B.
2. 'Sunny Zara' has entire, obovate to lanceolate leaves with obtuse tip, 3–5 cm long and 2–3 cm wide, while the leaves of 'Sunny Sonja' are obovate with acuminate tip, 8 cm long and 3.2 cm wide.
3. 'Sunny Zara' is globular and more compact than the plants of the cultivar 'Sunny Sonja'. The plant height and spread of 'Sunny Zara' is 20 cm, while the plant height of 'Sonny Sonja' is 38 cm and spread is 67 cm.

BRIEF DESCRIPTION OF THE PHOTOGRAPHS

The accompanying color photographs illustrate the overall appearance and details of flower form, color and structures of the new cultivar, showing the colors as true as it is reasonably possible to obtain in color reproductions of this type. Colors in the photographs may differ slightly from the color values cited in the detailed botanical description, which more accurately describe the actual colors of the new *Osteospermum.*

The first photograph is a side view of a typical flowering plant of 'Sunny Zara' as grown in an 11 cm pot.

The second photograph is a top view of a typical flowering plant of 'Sunny Zara'.

The third photograph is a close-up of the composite flower of 'Sunny Zara'.

The fourth photograph shows the flowers and leaves of 'Sunny Zara' (in the fourth photograph, 'Sunny Zara' is labelled by its breeder's reference no. 21.017.00).

DETAILED BOTANICAL DESCRIPTION

In the following description, color references are made to The Royal Horticultural Society Colour Chart, 4$^{th}$ edition, where general terms of ordinary dictionary significance are used. Plants were grown under greenhouse conditions. Plants used for this description were grown for about 20 weeks after cutting.

Plant description:

*Form.*—Perennial plant with globular plant habit. Composite flower heads. Freely branching with lateral flowering branches forming at every node; dense and bushy.

*Crop time.*—After rooting, about 20 weeks are required to produce finished flowering plants in 11 cm pots.

*Plant height* (*soil level to top of plant plane*).—About 20 cm.

*Plant spread.*—About 20 cm.

*Vigor.*—Vigorous growth rate.

*Time to initiate roots.*—About 10 to 14 days at 18 to 21° C. in tunnels in a greenhouse.

*Root description.*—Fine, well branched.

*Foliage description.*—Leaves alternate, single, slightly lobed, brochidodromus venation.

*Length.*—3–5 cm. Width: About 2–3 cm. Shape: Obovate to lanceolate. Apex: Obtuse. Base: Attenuate. Margin: Broadly dentate. Texture: Smooth, glabrous, shiny. Scattered short, stiff hairs. Color: Young foliage, upper surfaces 144A, yellow-green and lower surface 148B. Mature foliage, upper surface 137A and lower surface 148A. Venation, 148A lower surface (veins not visible on upper surface).

Flower description:

*Flower arrangement and shape.*—Tubular disk and petalled ray flowers in composite daisy capitulae; with 15 parted involucre. 9–10 cm sturdy peduncles.

*Natural flowering season.*—Continuous throughout April to September in temperate regions. Season can be extended by vernalization and long day treatments.

*Flower longevity on the plant.*—5 to 10 days; longevity of individual flowers is highly dependent on temperature and light conditions. Flowers persistent, petals folding and withering slowly.

*Inflorescence diameter.*—About 4–5 cm.

*Buds.*—Length: 0–10 mm. Diameter: 0–10 mm. Shape: Globular. Rate of Opening: 3 per plant per week. Color: yellow-green, 144B.

*Flowers.*—Disk petal number: 50–60 fused at base. Disk petal length: 1 mm free tip, size of entire petal (fused) 3 mm. Disk diameter: 14 mm. Disk petal shape: Free parts attenuate. Disk petal color: Silver, 100C (both surfaces). Ray petal number: 16. Petal Length: Ray petals: About 25–28 mm. Width: About 8 mm. Elliptic shape, acute ray petal lobes. Ray petal color: Upper surfaces red-purple 59C with stripes of N57B; underside N86C, base N155A. Petal texture (both surfaces): Smooth.

*Phyllaries.*—Number: About 14. Length: 15–20 mm. Shape: Overall lancelolate; basally fused; apically acute. Margin: Entire, somewhat translucent. Color: Outside, yellow-green, 144B; inside, light yellow-green, 145D. Texture: Smooth, glabrous.

*Peduncle.*—Medium strength. Length: About 9–10 cm. Diameter: About 2 mm. Color: 144C yellow-green. Texture: Hispidolous.

*Receptacle.*—Size (diameter): 12 mm. Outer color (abaxial), 144B, yellow-green. Inner color (adaxial): 145D, light yellow-green.

Reproductive organs:

*Stamen.*—Number 5.

*Anthers.*—Linear fused, Length: 2 mm. Color: 202A, black.

*Filament.*—Length: 3 mm.

*Pollen.*—RHS 26A orange.

*Pistil.*—Number: 1. Length: 4 mm.

*Stigma.*—Shape: Brush-like; Color: RHS 16C, yellow-orange.

*Style.*—Length: 2 mm.

*Seed.*—Length: About 2–3 mm. Diameter: About 1 mm. Color: 199C, grey-brown.

*Fruit.*—Shape: Oblong, achene with ridges. Length: 3 mm. Diameter: 1 mm. Color: 199C, grey-brown.

*Disease/pest resistance.*—No specific susceptibility or resistance observed.

*Disease susceptibility.*—None observed.Weather tolerance: Plants of the new *Osteospermum* have exhibited good tolerance to draught, rain and wind, with low temperature tolerance to 1° C.

I claim:

1. A new and distinct cultivar of *Osteospermum* plant named 'Sunny Zara', as illustrated and described herein.

* * * * *

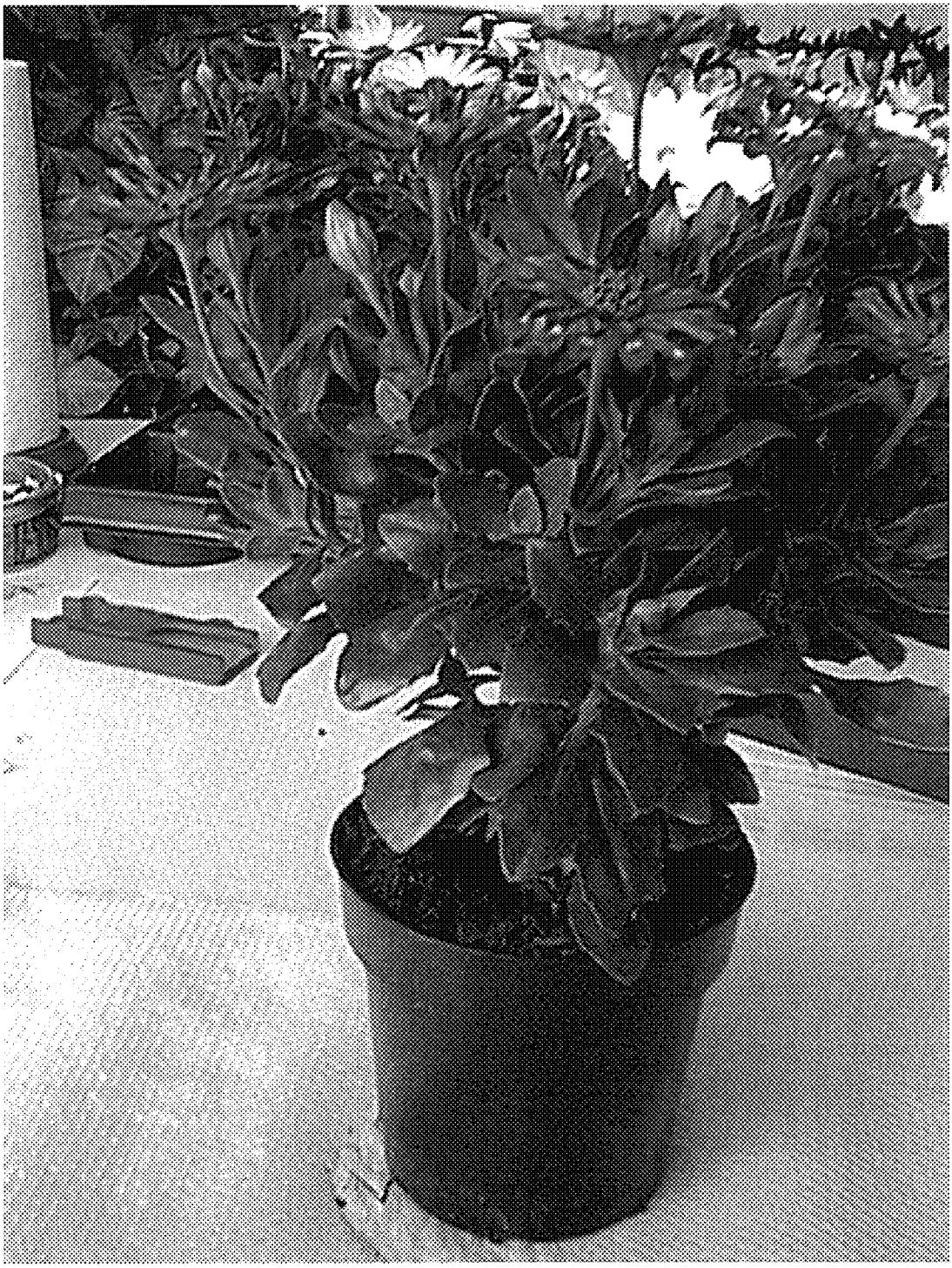

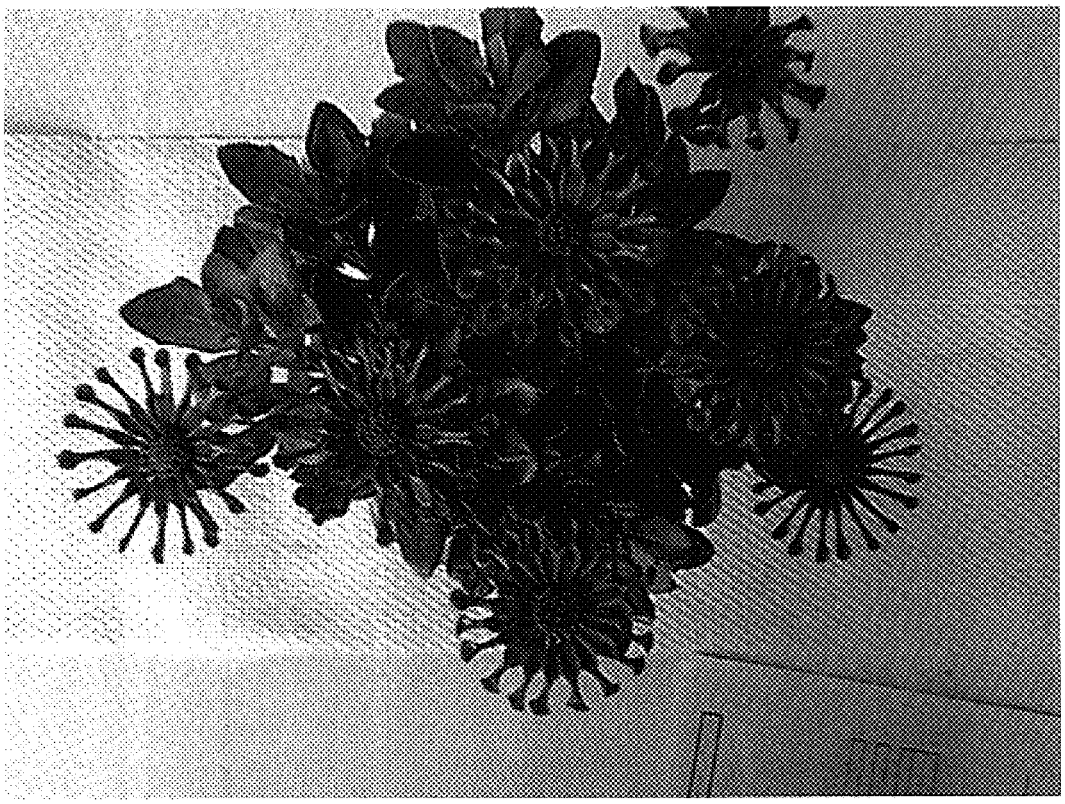

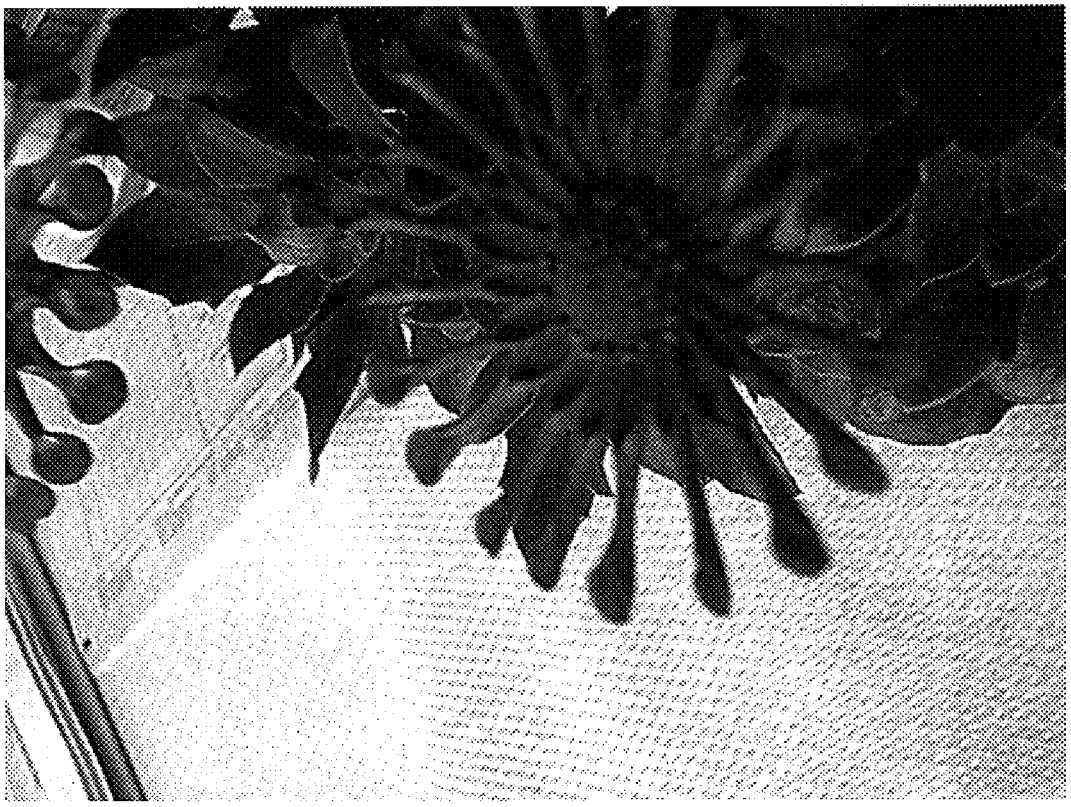

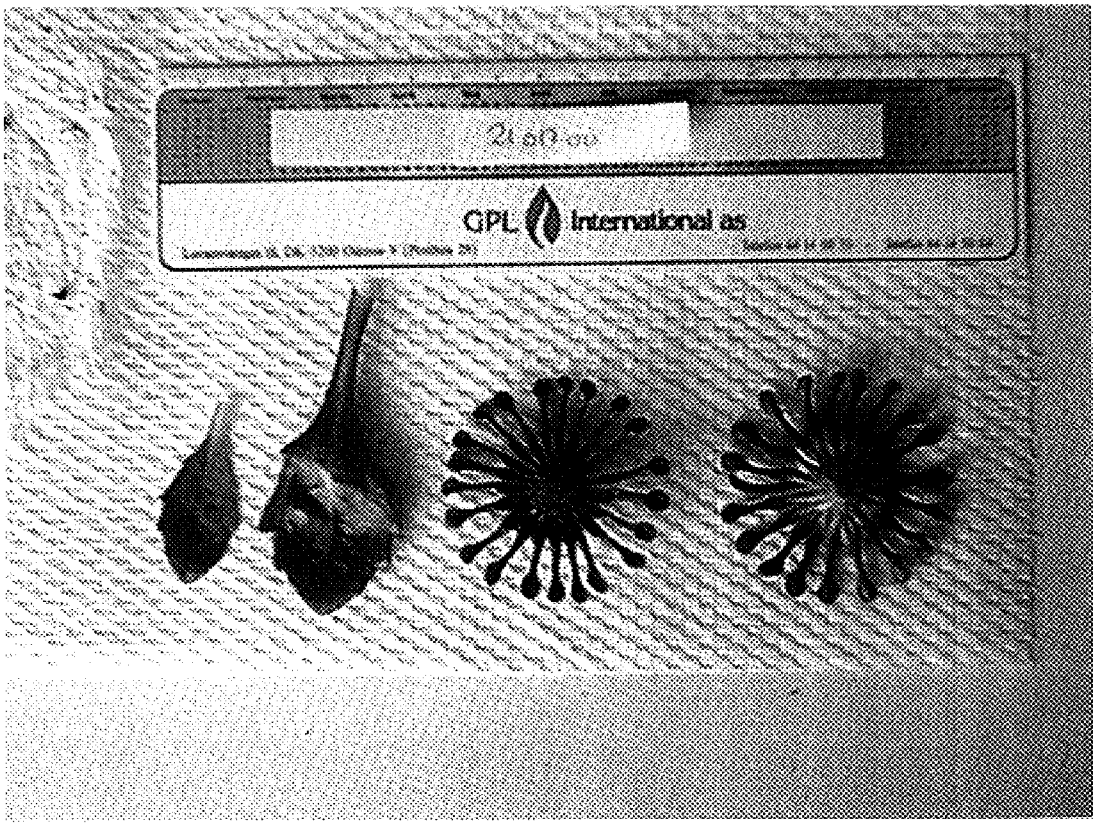
GPL International as